United States Patent [19]

Schwiesow

[11] Patent Number: 5,227,636
[45] Date of Patent: Jul. 13, 1993

[54] DUAL PATH ULTRAVIOLET HYGROMETER

[75] Inventor: Ronald L. Schwiesow, Boulder, Colo.

[73] Assignee: University Corporation for Atmospheric Research, Boulder, Colo.

[21] Appl. No.: 760,722

[22] Filed: Sep. 16, 1991

[51] Int. Cl.$^5$ .............................................. G01N 21/25
[52] U.S. Cl. ................................. 250/373; 250/345; 356/437
[58] Field of Search ................ 250/252.1 A, 373, 339, 250/343, 349, 351, 345, 573, 575; 356/437; 73/335.01, 335.02

[56] References Cited

U.S. PATENT DOCUMENTS

| | | | |
|---|---|---|---|
| 3,306,156 | 2/1967 | Glasser et al. | 250/373 X |
| 3,364,351 | 1/1968 | Palmer et al. | 250/343 X |
| 3,483,378 | 12/1969 | Murray | 250/351 |
| 3,636,768 | 1/1972 | Tinet et al. | 73/336.5 |
| 4,514,257 | 4/1985 | Karlsson et al. | 250/373 X |
| 4,526,034 | 7/1985 | Campbell et al. | 250/504 R X |
| 4,535,241 | 8/1985 | Eberhardt | 250/343 X |
| 4,627,284 | 12/1986 | Gersh et al. | 250/373 X |
| 4,673,812 | 6/1987 | Yoneda | 250/252.1 A |
| 4,990,781 | 2/1991 | Heller | 250/339 X |

OTHER PUBLICATIONS

Andre Zuber and Georg Witt; "Optical hygrometer using differential absorption of hydrogen Lyman–αradiation"; Aug. 1, 1987/vol. 26, No. 15/Applied Optics; pp. 3083–3089.

Primary Examiner—Constantine Hannaher
Assistant Examiner—Edward J. Glick
Attorney, Agent, or Firm—Duft, Graziano & Forest

[57] ABSTRACT

The dual path ultraviolet hygrometer makes use of two narrow spectrum light beams of different wavelengths, both of which are transmitted along two geometrically similar paths to measure and compensate for the presence of contaminants and to more precisely measure the water vapor content in the air samples. A first one of these optical wavelengths is highly absorbed by water vapor while the second optical wavelength is only slightly absorbed by water vapor. Both of these generated narrow band light beams are split so that two pairs of light beams are produced. Beams of both wavelengths are transmitted along the first optical path, which traverses the air sampling chamber. By measuring the differential absorption between the two light beams along this first optical path, the water vapor content of the air sample within the air sampling chamber is precisely measured by correcting for contaminant absorption. The second beam of each pair of each wavelength is transmitted along a second optical path, which is geometrically similar to the first optical path to measure the strength of each source. By measuring the differential and received intensities of the two sets of light beams, the level of contaminants in the air sampling chamber for both of the light beams can be determined, since the second wavelength is subject primarily to contamination. Therefore, the contamination in the air sampling chamber can be individually compensated at both of the wavelengths to obtain water vapor concentration measurements of greater precision.

12 Claims, 4 Drawing Sheets

5,227,636

DUAL PATH ULTRAVIOLET HYGROMETER

FIELD OF THE INVENTION

This invention relates to hygrometers and, in particular, to an improved hygrometer that uses two wavelengths of ultraviolet light as well as two geometrically similar optical transmission paths to precisely measure the water vapor content of the air sample and also determine the level of contaminants within the sampling path of the hygrometer to minimize the measurement errors caused by these contaminants.

PROBLEM

It is a problem in the field of hygrometers to precisely measure the water vapor content of the air sample, especially in the presence of contaminants (such as water droplets or salt crystals) within the sampling equipment. Hygrometers are used in airborne meteorological measurements to determine the amount of water vapor and its flux in the atmosphere in a predetermined location. Hygrometers generally accomplish this function by measuring the absorption of a single predetermined wavelength of light transmitted through an air sample. The optical wavelength is selected to be heavily absorbed by water vapor so that the amount of absorption of the transmitted light is directly correlated to the quantity of water vapor in the air sample. A significant difficulty with this arrangement is that contaminants in the air samples may also flow through and increase the absorption of the light, distorting the measurements that are taken. This is a major problem with prior art hygrometers. In addition, the use of a single light beam renders the measurements susceptible to inconsistency due to variations in lamp intensity, discharge geometry, and drifts in detector electronics.

One example of a prior art hygrometer design is illustrated in U.S. Pat. No. 3,636,768, which discloses an infrared hygrometer that produces two presumed identical infrared light beams. One of these infrared light beams passes through an enclosure containing a dry air reference while a second infrared light beam passes through an identical enclosure containing an air sample whose water vapor content is to be measured. The difference in absorption of the two infrared light beams transversing the two optical paths is indicative of the water vapor content of the air sample.

A second hygrometer design is illustrated in U.S. Pat. No. 4,627,284 which discloses an ultraviolet hygrometer that produces a single beam of ultraviolet light having a broad wavelength spectrum. The beam of ultraviolet light is passed through the air sample and then filtered into a first wavelength region that is heavily absorbed by water vapor and a second wavelength region that is weakly absorbed by water vapor. The difference between the two received light intensities is indicative of the concentration of water vapor in the air sample.

One difficulty with prior art hygrometers that use broad spectrum light beams is that absorption of the different wavelengths of light in the light beam varies, thereby introducing a certain amount of error in the measured average light intensity. Another difficulty is that contaminants contained in the air sample increase the absorption of the transmitted light, which provides a second error component in the output signal. In certain environmental conditions, the contaminants can be a significant source of error in the water vapor concentration measurements.

SOLUTION

The above described problems are solved and a technical advance achieved in the field by the dual path ultraviolet hygrometer of the present invention. The dual path ultraviolet hygrometer makes use of two narrow spectrum light beams at different wavelengths, both of which are transmitted along two geometrically similar optical paths to measure and compensate for the presence of contaminants and to more precisely measure the water vapor content in the air samples. A first one of these optical wavelengths is highly absorbed by water vapor while the second optical wavelength is only slightly absorbed by water vapor. Both of these generated narrow band light beams are split so that two pairs of light beams are produced. Beams of both wavelengths are transmitted along the first optical path, which traverses the air sampling chamber. By measuring the differential absorption between the two light beams along this first optical path, the water vapor content of the air sample within the air sampling chamber is precisely measured by correcting for contaminant absorption. The second beam of each pair at each wavelength is transmitted along a second (reference) optical path, which is geometrically similar to the first optical path to measure the strength of each source. By measuring the differential and received intensities of the two sets of light beams, the level of contaminants in the air sampling chamber for both of the light beams can be determined, since the second wavelength is subject primarily to contamination. Therefore, the contamination in the air sampling chamber can be individually compensated at both of the wavelengths to obtain water vapor concentration measurements of greater precision.

Therefore, by using two precisely defined wavelengths of light and two geometrically similar light transmission paths, the water vapor concentration can be more precisely measured due to the differential in absorption of the two wavelengths of light in the air sampling chamber, which measured absorptions are individually compensated by measuring the source strength at both of these wavelengths using the second light path in the hygrometer.

DETAILED DESCRIPTION

The dual path ultraviolet hygrometer makes use of two narrow spectrum light beams at different wavelengths, both of which are transmitted along two geometrically similar optical paths to measure and compensate for the presence of contaminants and to more precisely measure a component concentration in a gas sample. A first one of these optical wavelengths is highly absorbed by the component while the second optical wavelength is only slightly absorbed by the component.

Both of these generated narrow band light beams are split so that two pairs of light beams are produced. Beams of both wavelengths are transmitted along the first optical path, which traverses the gas sampling chamber. By measuring the differential absorption between the two light beams along this first optical path, the component concentration of the gas sample within the gas sampling chamber is precisely measured by correcting for contaminant absorption. The second beam of each pair at each wavelength is transmitted along a second (reference) optical path which is geometrically similar to the first optical path to measure the strength of each source. By measuring the differential and received intensities of the two sets of light beams, the level of contaminants in the sampling chamber for both of the light beams can be determined, since the second wavelength is subject primarily to contamination. Therefore, the contamination in the sampling chamber can be individually compensated at both of the wavelengths to obtain component concentration measurements of greater precision.

SYSTEM ARCHITECTURE

Figure 1:
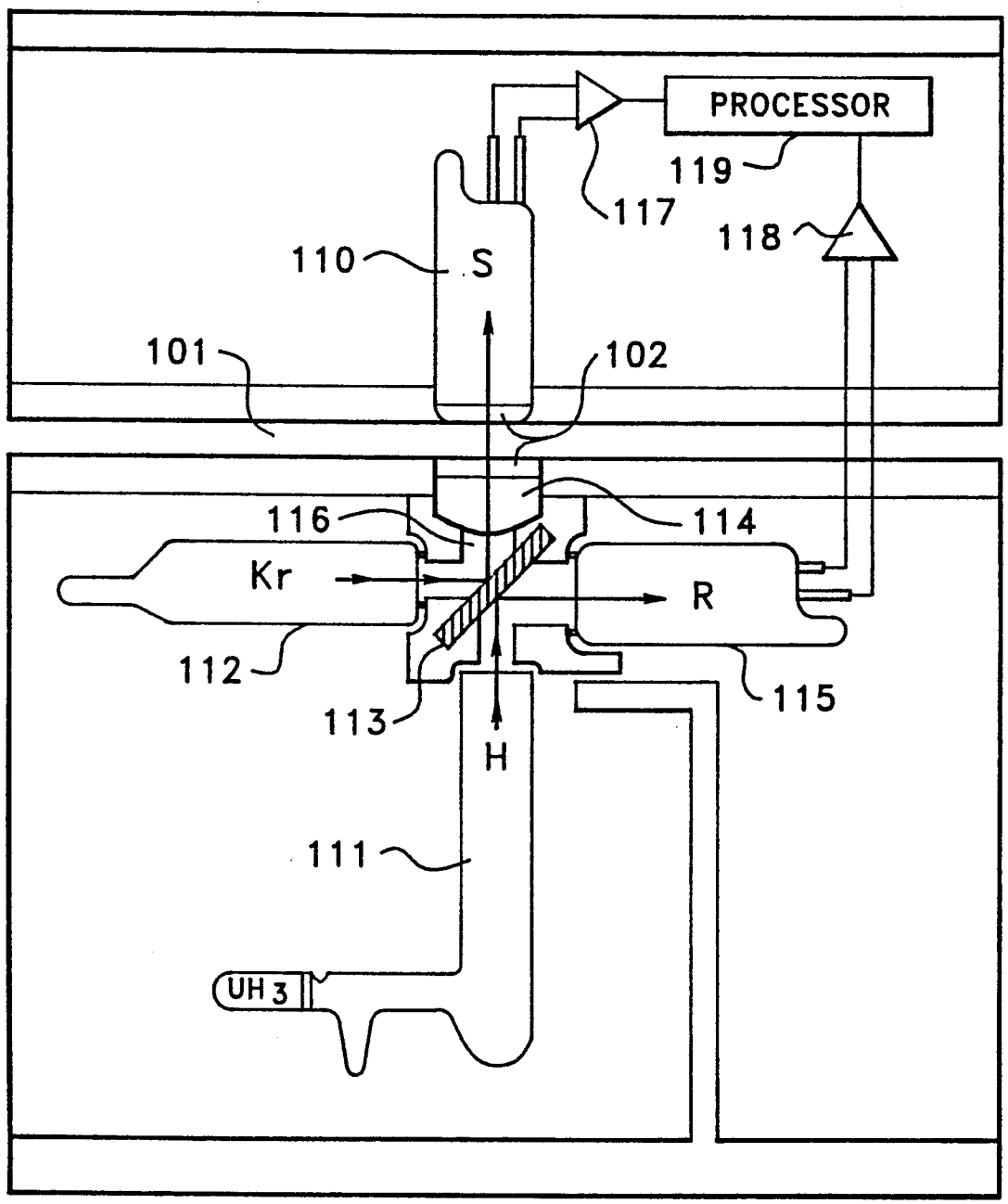
FIG. 1 illustrates in block diagram form the overall architecture of the dual path ultraviolet hygrometer of the present invention.

FIG. 1 illustrates in block diagram form the overall architecture of the dual path ultraviolet hygrometer of the present invention. This apparatus is used to measure water vapor content of an air sample. In FIG. 1 the air samples are introduced into an air sampling chamber 101 on a continuing basis in order to measure the water vapor content of these air samples. In a typical application, the hygrometer is carried aloft outside an aircraft to sample the water vapor content of the atmosphere at a particular site. The optical path length across air sampling chamber 101 is of precise dimensions in order that a predetermined distance through air is used for the measurement process. Disposed along one side of the air sampling chamber is located at least one light detector 110 which measures the intensity of the ultraviolet light that is transmitted through the air sample contained in the air sampling chamber 101. A single light detector 110 can be used if the two light beams transmitted through the air sampling chamber 101 are alternatively pulsed on and off so that only a single light beam is incident on the light detector 110 at a particular moment. If both light beams are transmitted concurrently, two light detectors are needed in order to differentially measure the intensity of each of the light beams.

The light beams are generated by use of two light sources 111, 112, each of which produces a light beam having a very narrow wavelength spectrum in order that the absorption across all wavelengths in each light beam remains constant. The ultraviolet lamps 111, 112 each produce a single spectral line in the region of interest and these lines are compared with the absorption spectra of the water vapor molecule which arises from an electronic transition. The principal wavelength produced by the first ultraviolet lamp 11 is the Lyman-$\alpha$ line of hydrogen (H) at 121.6 nm and the secondary wavelength produced by the second ultraviolet lamp 112 is at 123.6 nm from the spectrum of krypton (Kr). Ultraviolet lamps 111, 112 are the electrodeless discharge type while the light detector 110 is a standard nitric oxide (NO) ionization cell.

The optics and the source and detector electronics are mounted in a streamlined housing exposed to the airstream. Air sampling chamber 101 consists of a channel through the housing to allow the passage of air for sampling. Optical components are also shown in FIG. 1.

The reference detector 115 (R), the collimating lens 114, and the two ultraviolet lamps (H and Kr) 111, 112 are mounted in four sides of a sealed cube 116, filled with $N_2$ so that the reference detector 115 views the two ultraviolet lamps 111, 112 through a nonabsorbing gas. The magnesium fluoride ($MgF_2$) optical beam splitter 113 is situated inside the cube 116 at a 45° angle. The focal length of the collimating lens 114 is chosen so that its focal point lies within the discharge volumes of the lamps 111, 112. This provides an approximately collimated beam across the air sample chamber 101. The signal detector (S) 110 is mounted with its window 102 flush with the wall on the opposite side of the air sample chamber 101.

The ultraviolet lamps 111, 112 are sealed gaseous discharge lamps excited by radio-frequency (rf) fields at 100-200 MHz. The H lamp 111 is filled with Ne and has an arm containing U and $UH_3$ at a controlled temperature while the Kr lamp 112 is filled with Kr.

The light detectors 110, 115 are nitric oxide (NO) ionization cells consisting of glass tubes filled with NO. Ultraviolet light enters through $MgF_2$ windows that are affixed with epoxy seals. The light detectors 110, 115 have cylindrical geometry with a central, axial conductor and an outer cylindrical conductor. The outer conductor is biased and the conduction current through the gas resulting from photoionization is collected at the central conductor. The NO cell acts as a current source, so a current-to-voltage amplifier 117, 118 is connected to each light detector 110, 115. The signals output by the amplifiers 117, 118 are processed by processor 119 to produce the indication of water vapor content in the air sample.

PRINCIPLES OF OPERATION

Figure 2:
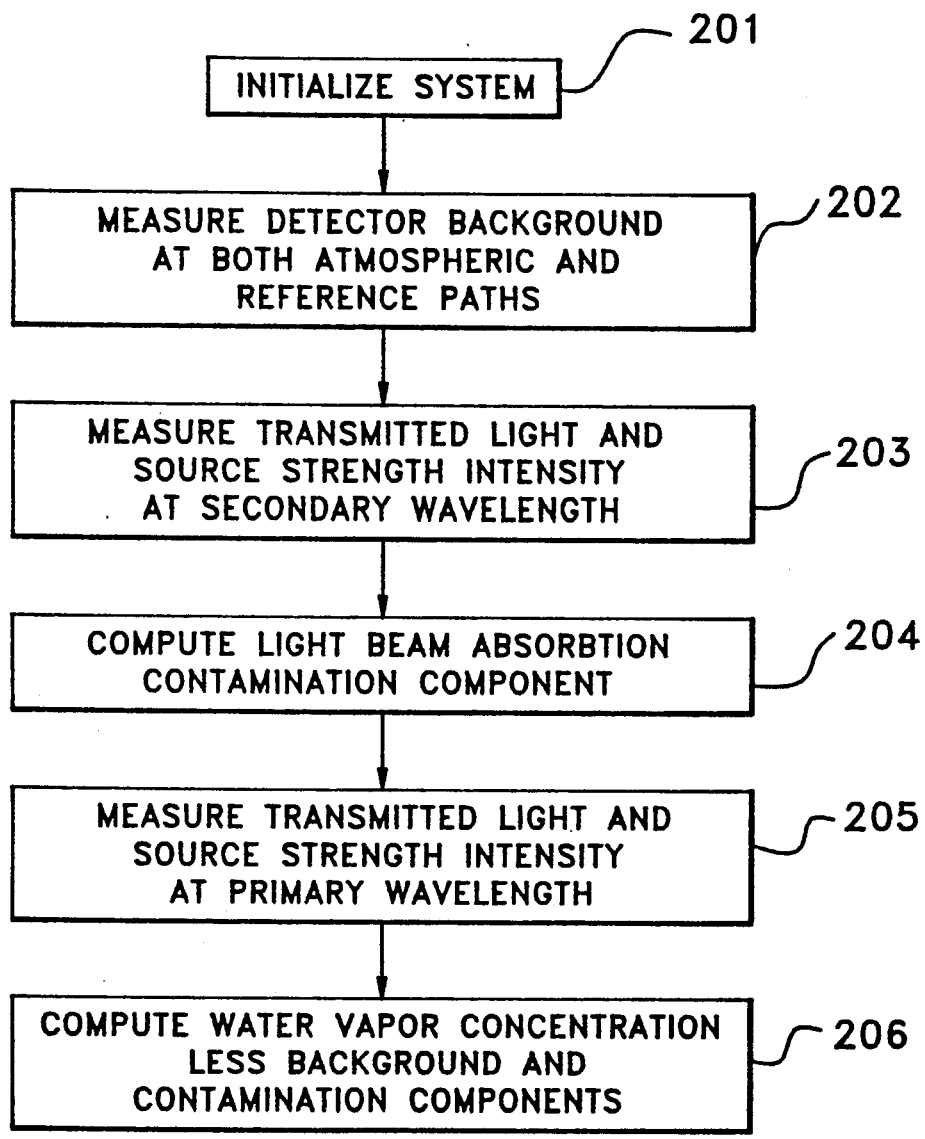
FIG. 2 illustrates in flow diagram form the operational steps taken by the hygrometer to process the light samples.

FIG. 1 shows the optical layout of the instrument and FIG. 2 illustrates in flow diagram form the operational steps used to analyze air samples therein. The light beam output from each of the two lamps 111, 112 (labeled H and Kr) is divided, one at a time, by an optical beam splitter 113 so that part of each light beam falls on the reference detector 115 (R), and part on the signal detector 110 (S). The reference detector 115 views the ultraviolet light beams through a nonabsorbing reference path that is geometrically similar to the sample path, while the signal detector 110 views the ultraviolet light beams through the sample path.

At step 201, the system is initialized. At step 202 both lamps are off and any residual background signal on detectors 110, 115 is determined. With only lamp 112 turned on, the effect of contamination in chamber 101 or on windows 102 is determined in steps 203 and 204. Then, with only lamp 111 turned on, the effect of water vapor absorption in chamber 101 is determined in step 205. At step 206 the results of the six measurements (three values from each of two detectors) are combined to yield the desired water vapor concentration. The three measurement conditions (lamp off, 112 on, 111 on) may be done in any order leading to step 206. Details of the process are discussed below. Before measurements are made, for each of the ultraviolet lamps 111, 112, an intercalibration of the two detectors 110, 115 is performed with a nonabsorbing gas in the air sampling chamber 101. For a given lamp, this calibration ratio of the two detector outputs, when combined with a measurement of the reference detector output 115 at the time the atmospheric path is sampled, enables one to compute the maximum possible output from the signal detector 110. Any smaller value is due to absorption by gases (or particles) in the air sampling chamber 101 or by contamination on the windows 102.

The ideal choice for the second wavelength would be one that is not absorbed by water vapor at all, but which suffers precisely the same absorption by window or path contamination as does Lyman-α radiation. Then any reduction in the output from the signal detector as measured at step 203 for this second lamp would be due to window contamination as computed at step 204. The output of the signal detector for the Lyman-α light as measured at step 205 could then be adjusted for the same fractional loss due to window contamination at step 206. In practice, any slight absorption by water vapor at the second line simply results in a decrease in sensitivity for this differential technique, and it is accommodated in a straightforward fashion, since it is the cross-section difference that appears in the analysis.

Figure 3:
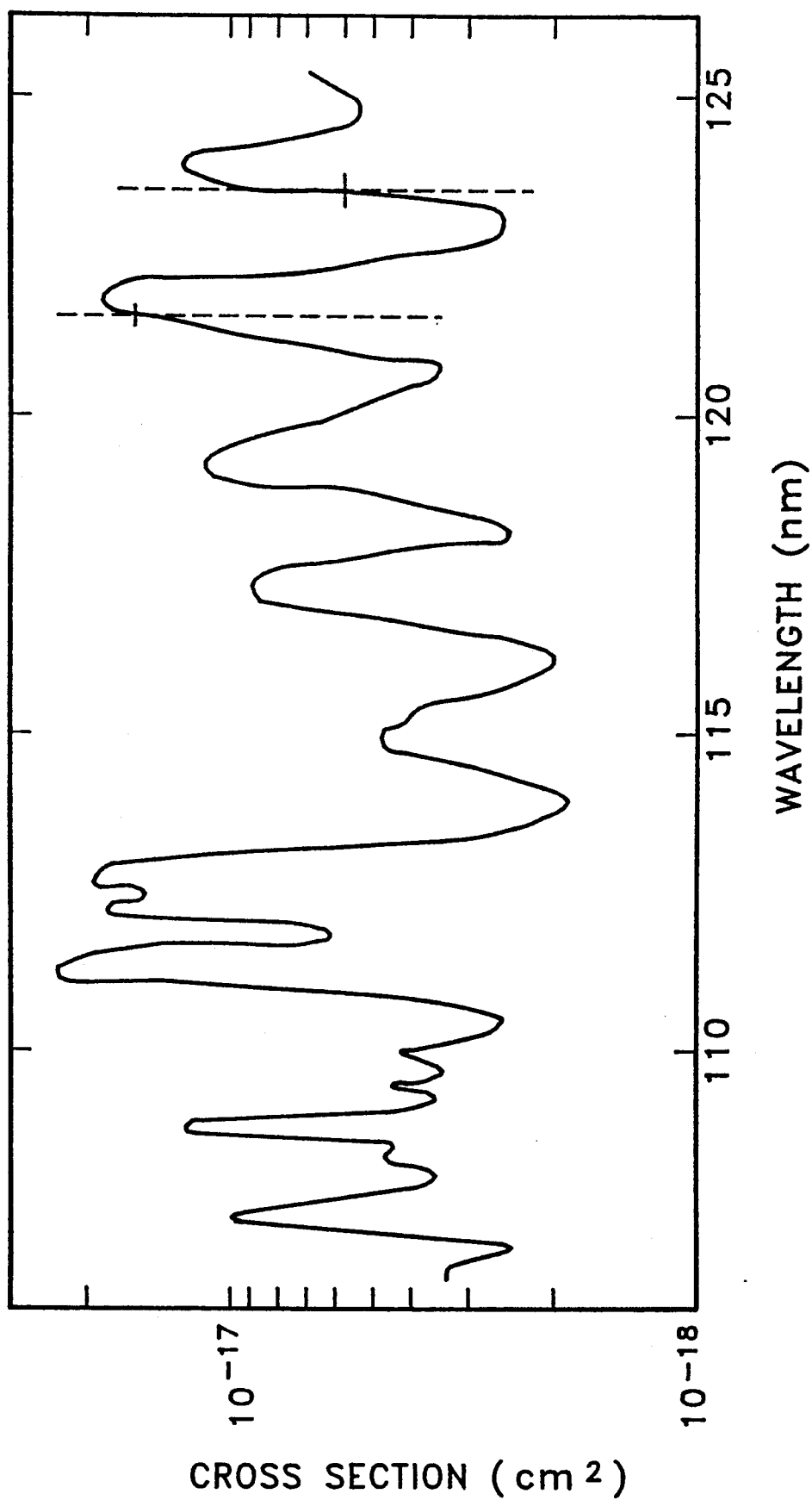
FIG. 3 illustrates in graphical form the spectrum of water vapor.
Figure 4:
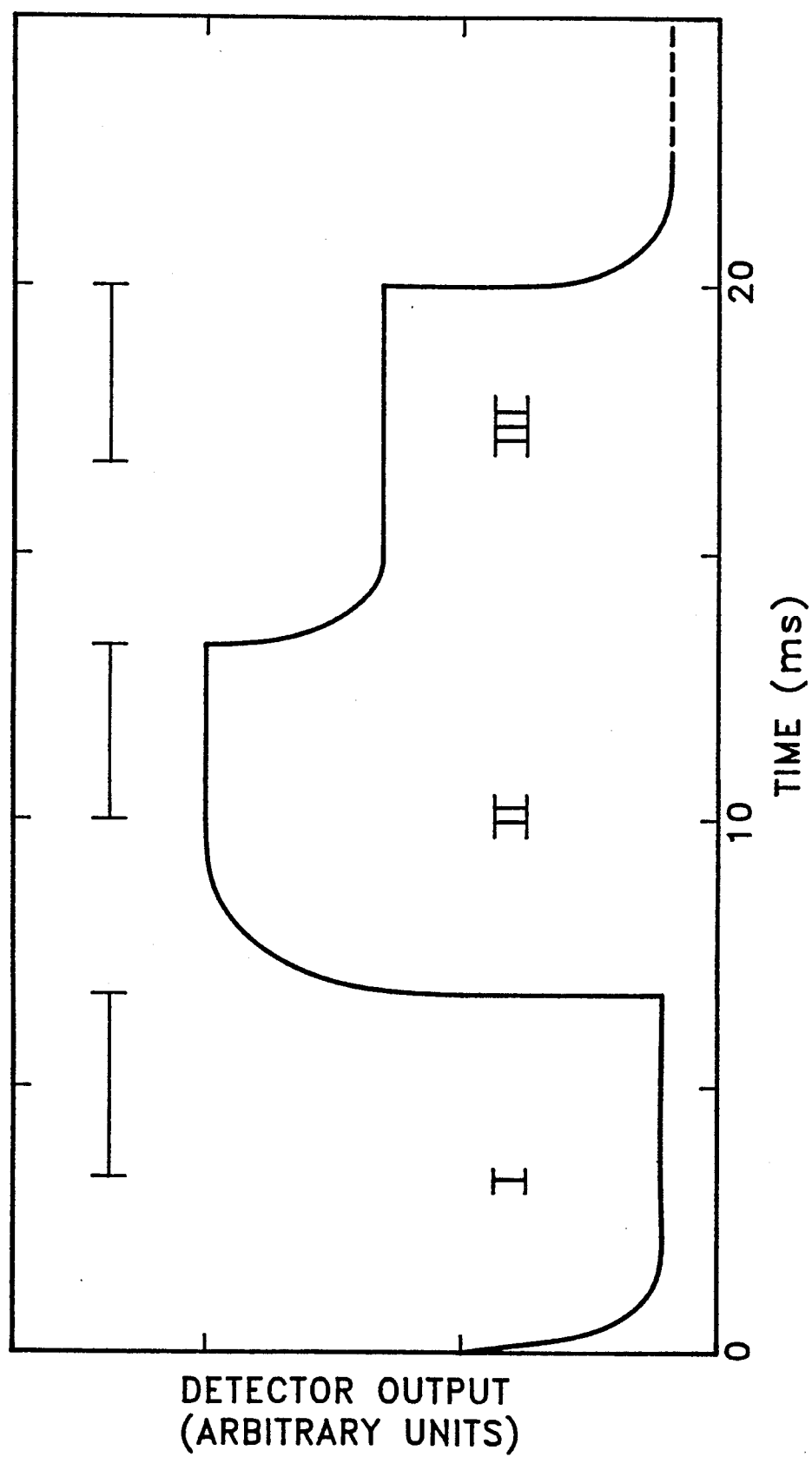
FIG. 4 illustrates in graphical form the output produced by each light detector over time.

FIG. 3 shows the spectrum of water vapor in the region of the Lyman-α line. The absorption results from electronic transitions in the molecule, so the absorption lines are much more widely spaced than are vibration-rotation transitions, which occur in the infrared. The Kr line for the secondary reference wavelength can be used in practice for two reasons. First, it is close to the Lyman-α line (2.0 nm away), so it suffers equal attenuation by the contaminants on the window 102. The closeness of the two wavelengths of ultraviolet light also allows ionization detectors to be used as light detectors 110, 115. Secondly, the absorption by water vapor of the Kr line is only 27% of that at the Lyman-α wavelength so there is only a 27% loss in sensitivity. Pressure and temperature are accurately measured in sampling chamber 101, and the fraction of oxygen in the dry component of air is assumed constant, so the correction for oxygen is easily performed.

The output voltage generated by the light detectors 110, 115 is a linear function of the light intensity received by the light detectors 110, 115 and is given by:

$$V = \Delta V + k I e^{-\tau}, \quad (1)$$

where $\Delta V$ is the offset determined in step 202, I is the light intensity incident on the sample volume, k is a constant of proportionality, and $\tau$ is the optical depth. The optical depth is due to $H_2O$, $O_2$, and contamination on the windows 102. The effects of other gases are negligible. The optical depth may be written as $$\tau_1(air) = n(H_2O)\sigma_1(H_2O)L + n(O_2)\sigma_1(O_2)L + b_1. \quad (2)$$

The subscript '1' denotes the Lyman-α wavelength, lamp 111, n(A) is the concentration for species A, $\sigma_1(A)$ is its absorption cross section at $\lambda_1 = 121.6$ nm, L is the path length for the light through air sampling chamber 101, and $b_1$ is the extinction due to the contamination on the window 102. The measured optical depth is obtained from the measurements 202, 203, and 205, with the aid of the intercalibration, as previously described. An expression similar to equation (2) holds for the second (Kr) wavelength, lamp 112 with subscript 2. We assume the same blockage at both wavelengths, $b_1 = b_2$, although a known ratio could be used instead.

In one embodiment of the invention, the final working equation is:

$$n_a(H_2O) = \left(\frac{P_a}{P}\right)^{\frac{1}{\gamma}} \frac{1}{\Delta\sigma(H_2O)L} \frac{1}{1-y}(\tau_1 - \tau_2) - \frac{y}{1-y}\frac{P_a}{k_B T_a}. \quad (3)$$

Here, subscript a refers to ambient conditions, and the pressure ratio term corrects for pressure difference between the ambient atmosphere and the sampling chamber 101. $\Delta\sigma(A)$ is the difference in cross sections at the two wavelengths for constituent A, and y is the oxygen correction term, $$y = f'(O_2)\frac{\Delta\sigma(O_2)}{\Delta\sigma(H_2O)} \quad (4)$$

where $f'(O_2)$ is the mole fraction of oxygen in dry air, a known value, $1/\gamma = 0.71$ for dry air, and $k_B$ is the Boltzmann constant from the ideal gas law.

While a specific embodiment of this invention has been disclosed, it is expected that those skilled in the art can and will design alternate embodiments of this invention that fall within the scope of the appended claims.

I claim:

1. Apparatus for measuring the concentration of a component contained in a sample of a gas, comprising:
    sampling chamber means for containing said gas sample;
    first light source means for generating a beam of light at a wavelength that is heavily absorbed by said component;
    second light source means for generating a beam of light at a wavelength that is lightly absorbed by said component;
    means for splitting said light beam from each of said first and said second light source means into first and second pairs of light beams, each of said first and second pairs of light beams including a light beam from said first and said second light source means;
    means for transmitting said first pair of light beams comprising a beam of light from said first and second light source means through said gas sample contained in said sampling chamber;
    means for measuring the intensity of said beam of light from said first light source means transmitted through said gas sample contained in said sampling chamber to identify the concentration of said component in said gas sample;
    means for measuring the intensity of said beam of light from said second light source means transmitted through said gas sample contained in said sampling chamber to identify light beam absorbing contamination in said sampling chamber;
    light detector means, located in a light path geometrically similar to a light path from said first and second light source means through said sampling chamber to said intensity measuring means that carries said first pair of light beams, for measuring the intensity of said second pair of light beams from said first and second light source means through said similar light path absent said gas sample;
    means for correcting said measured light intensity for said first and second light beams in said first pair of light beams through said gas sample by said measured light intensity for said first and second light beams of said second pair of light beams through said light path absent said gas sample; and means for correcting said measured transmitted light intensity from said first light source means by said measured light beam absorbing contamination in said sampling chamber.

2. The apparatus of claim 1 wherein said first and said second light source means generate light beams of narrow wavelength spectrum.

3. The apparatus of claim 1 further comprising:

means for sequentially activating said first and said second light source means to produce alternating periods of light from said first and said second light source means; and wherein said measuring means includes:

means for determining the differential between the intensity of said light beam received from said first light source means and said second light source means, means for scaling said determined differential to compute said concentration of said component in said gas sample.

4. The apparatus of claim 1 further comprising:

means for activating said intensity measuring means absent said light beams from said first and second light source means to measure ambient light intensity in said sampling chamber and leakage current in said intensity measuring means; and means for correcting said measured intensity of said beams of light from said first and second light source means by said measured ambient light intensity.

5. A hygrometer apparatus for measuring the water vapor concentration of an air sample, comprising:

air sampling chamber means for containing said air sample;

first light source means for generating a beam of ultraviolet light at a wavelength that is heavily absorbed by water vapor;

second light source means for generating a beam of ultraviolet light at a wavelength that is lightly absorbed by water vapor;

means for splitting said light beam from each of said first and said second light source means into first and second pairs of light beams, each of said first and second pairs of light beams including a light beam from said first and said second light source means;

means for transmitting said first pair of light beams comprising a beam of light from both said first and second light source means through said air sample contained in said air sampling chamber;

means for measuring the intensity of said beam of light from said first and second light source means transmitted through said air sample contained in said air sampling chamber to determine said water vapor concentration in said air sample;

means for measuring the intensity of said beam of light from said second light source means transmitted through said air sample contained in said air sampling chamber to determine light beam absorbing contamination in said air sampling chamber;

light detector means, located in a light path geometrically similar to a light path from said first and second light source means through said air sampling chamber to said intensity measuring means that carries said first pair of light beams, for measuring the intensity of said second pair of light beams from said first and second light source means through said similar light path absent said air sample;

means for correcting said measured light intensity for said first and second light beams through said air sample by said measured light intensity for said first and second light beams through said light path absent said air sample; and means for correcting said measured transmitted light intensity from said first light source means by said measured light beam absorbing contamination in said air sampling chamber.

6. The apparatus of claim 5 wherein said first and said second light source means generate light beams of narrow wavelength spectrum.

7. The apparatus of claim 5 further comprising:

means for sequentially activating said first and said second light source means to produce alternating periods of light from said first and said second light source means; and wherein said measuring means includes:

means for determining the differential between the intensity of said light beam received from said first light source means and said second light source means, means for scaling said determined differential to compute said water vapor concentration in said air sample.

8. The apparatus of claim 5 further comprising:

means for activating said intensity measuring means absent said light beams from said first and second light source means to measure ambient light intensity in said air sampling chamber and leakage current in said intensity measuring means; and means for correcting said measured intensity of said beams of light from said first and second light source means by said measured ambient light intensity.

9. A hygrometer apparatus for measuring the water vapor concentration of an air sample, comprising:

air sampling chamber means for containing said air sample;

first light source means for generating a beam of ultraviolet light at a wavelength that is heavily absorbed by water vapor;

second light source means for generating a beam of ultraviolet light at a wavelength that is lightly absorbed by water vapor;

means for splitting said light beam from each of said first and said second light source means into two pairs of light beams, each pair including a light beam from said first and said second light source means;

means for transmitting a first pair of light beams along a first light path from said first and second light source means through said air sample contained in said air sampling chamber;

means for measuring the intensity of said first pair of light beams transmitted through said air sample contained in said air sampling chamber to determine said water vapor concentration in said air sample and to identify the light beam absorbing contamination in said air sampling chamber;

light detector means, located in a second light path geometrically similar to said first light path and absent said air sample, for measuring the intensity of said light beams from said first and second light source means through said second light path absent said air sample; and means for correcting said measured transmitted light intensity of said first pair of light beams along said first light path by said measured intensity of said second pair of light beams along said second light path.

10. The apparatus of claim 9 wherein said first and said second light source means generate light beams of narrow wavelength spectrum.

11. The apparatus of claim 9 further comprising:

means for sequentially activating said first and said second light source means to produce alternating periods of light from said first and said second light source means; and wherein said measuring means includes:

means for determining the differential between the intensity of said light beam received from said first light source means and said second light source means, means for scaling said determined differential to compute said water vapor concentration in said air sample.

12. The apparatus of claim 9 further comprising:

means for activating said intensity measuring means absent said light beams from said first and second light source means to measure ambient light intensity in said air sampling chamber and leakage current in said intensity measuring means; and means for correcting said measured intensity of said beams of light in said first light path from said first and second light source means by said measured ambient light intensity.

* * * * *